United States Patent
Osaki et al.

(10) Patent No.: US 8,306,595 B2
(45) Date of Patent: Nov. 6, 2012

(54) BLOOD CONSTITUENT CONCENTRATION DETECTOR AND STARTER FOR TRANSPORTER

(75) Inventors: Rie Osaki, Anjo (JP); Mitsuo Inagaki, Okazaki (JP); Takashi Komura, Toyota (JP); Hirohiko Tatsumoto, Anjo (JP)

(73) Assignees: DENSO CORPORATION, Kariya (JP); Nippon Soken, Inc., Nishio (JP)

( * ) Notice: Subject to any disclaimer, the term of this patent is extended or adjusted under 35 U.S.C. 154(b) by 496 days.

(21) Appl. No.: 12/588,814

(22) Filed: Oct. 29, 2009

(65) Prior Publication Data
US 2010/0125187 A1    May 20, 2010

(30) Foreign Application Priority Data
Nov. 17, 2008  (JP) ................................ 2008-293356

(51) Int. Cl.
*A61B 5/00*    (2006.01)
(52) U.S. Cl. ....................................... 600/322
(58) Field of Classification Search .................... 600/322
See application file for complete search history.

(56) References Cited

U.S. PATENT DOCUMENTS

| | | | |
|---|---|---|---|
| 5,743,349 A * | 4/1998 | Steinberg ...................... | 180/272 |
| 2002/0016536 A1 | 2/2002 | Benni | |
| 2004/0083031 A1* | 4/2004 | Okezie ............................. | 701/1 |
| 2006/0063993 A1* | 3/2006 | Yu et al. ........................ | 600/322 |
| 2006/0131155 A1* | 6/2006 | Hopkins ........................ | 200/402 |
| 2006/0195024 A1 | 8/2006 | Benni | |
| 2008/0017800 A1 | 1/2008 | Benni | |
| 2009/0270701 A1* | 10/2009 | Osaki et al. ................... | 600/316 |
| 2010/0036592 A1* | 2/2010 | Osaki et al. ................... | 701/113 |
| 2011/0112386 A1* | 5/2011 | Maki et al. .................... | 600/322 |

FOREIGN PATENT DOCUMENTS

| | | |
|---|---|---|
| JP | A-57-45841 | 3/1982 |
| JP | A-05-176917 | 7/1993 |
| JP | A-2003-111750 | 4/2003 |
| JP | A-2003-265443 | 9/2003 |
| JP | A-2004-290545 | 10/2004 |
| JP | A-2005-351697 | 12/2005 |
| JP | A-2009-201895 | 9/2009 |

OTHER PUBLICATIONS

Office Action dated Aug. 17, 2010 issued from the Japanese Patent Office in corresponding patent application No. 2008-293356 (English translation enclosed).

* cited by examiner

*Primary Examiner* — Rodney Fuller
(74) *Attorney, Agent, or Firm* — Posz Law Group, PLC

(57) ABSTRACT

A blood constituent concentration detector includes: a detection portion having an optical window for measuring a blood constituent concentration of a part of a living body in an optical manner when the part of the living body is pressed on the detection portion; a load determination element for determining whether a load to the detection portion is equal to or larger than a first threshold, and smaller than a second threshold, wherein the second threshold is larger than the first threshold; and a measurement element for measuring the blood constituent concentration when the load determination element determines that the load to the detection portion is equal to or larger than the first threshold, and smaller than the second threshold.

9 Claims, 8 Drawing Sheets

BLOOD CONSTITUENT CONCENTRATION DETECTOR AND STARTER FOR TRANSPORTER

CROSS REFERENCE TO RELATED APPLICATION

This application is based on Japanese Patent Application No. 2008-293356 filed on Nov. 17, 2008, the disclosure of which is incorporated herein by reference.

FIELD OF THE INVENTION

The present invention relates to a blood constituent concentration detector and a starter for a transporter.

BACKGROUND OF THE INVENTION

Conventionally, a technique for measuring a concentration of a blood constituent noninvasively is well known. For example, JP-A-H05-176917 teaches the following technique. A near infrared light having a wavelength in a range between 780 nm and 1300 nm is irradiated on a human body, and then, an intensity of a transmitted light is measured. Based on the intensity of the transmitted light, a concentration of glucose in the human body is detected.

However, in the above technique, when a pressing force of a part of the human body as a measurement object is changed, the measurement result is changed. Thus, it is difficult to detect the concentration of glucose with high accuracy.

Thus, it is required for a blood constituent concentration detector to detect the blood constituent concentration with high accuracy.

Further, it is considered that an alcohol concentration in blood of a driver of a vehicle is measured, and a starter for a vehicle controls a starting operation of the vehicle based on determination whether the alcohol concentration in blood is smaller than a predetermined reference value.

In the above case, it is also required to detect the alcohol concentration in blood with high accuracy.

SUMMARY OF THE INVENTION

In view of the above-described problem, it is an object of the present disclosure to provide a blood constituent concentration detector. It is another object of the present disclosure to provide a starter for a transporter.

According to a first aspect of the present disclosure, a blood constituent concentration detector includes: a detection portion having an optical window for measuring a blood constituent concentration of a part of a living body in an optical manner when the part of the living body is pressed on the detection portion; a load determination element for determining whether a load to the detection portion is equal to or larger than a first threshold, and smaller than a second threshold, wherein the second threshold is larger than the first threshold; and a measurement element for measuring the blood constituent concentration when the load determination element determines that the load to the detection portion is equal to or larger than the first threshold, and smaller than the second threshold. The blood constituent concentration detector detects the blood constituent concentration with high accuracy.

According to a second aspect of the present disclosure, a starter for controlling start of a power source of a transporter based on operation of a starter switch by a driver, the controller includes: a detection portion having an optical window for measuring an alcohol concentration in blood of the driver in an optical manner; a load determination element for determining whether a load to the detection portion is equal to or larger than a first threshold, and smaller than a second threshold, wherein the second threshold is larger than the first threshold; a measurement element for measuring the alcohol concentration in blood when the load determination element determines that the load to the detection portion is equal to or larger than the first threshold, and smaller than the second threshold; a starting permission element for determining start permission of the power source based on determination whether the alcohol concentration in blood is smaller than a predetermined standard; and a starting controller for controlling the start of the power source. The starting controller starts the power source when the starting permission element determines the start permission of the power source, and the operation of the detection portion by the driver provides the operation of the starter switch by the driver.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS (First Embodiment)

Figure 1:
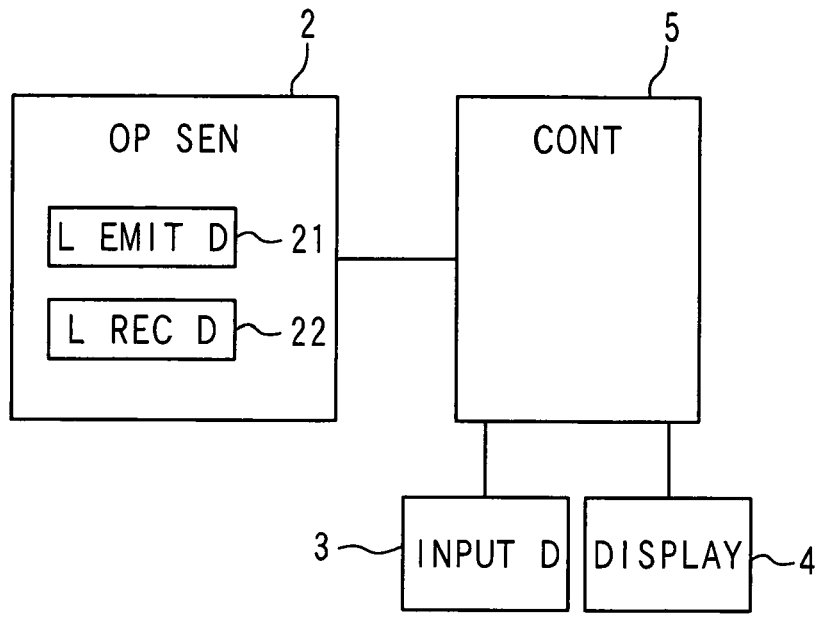
FIG. 1 is a block diagram showing a blood constituent concentration detector according to a first embodiment.

A blood constituent concentration detector according to a first embodiment is shown in FIG. 1. The detector includes an optical sensor 2, an operation input device 3, a display 4 and a controller 5.

The optical sensor 2 detects a pulse wave in a part of a human body in an optical manner. The sensor 2 includes a light emitting device 21 and a light receiving device 22. With using the light emitting device 21 and the light receiving device 22, the pulse wave in a tip of a finger of the human body is measured optically.

The operation input device 3 includes an operation device such as a switch and a mouse, and outputs a signal corresponding to operation of a user to the controller 5. The display 4 includes a display element such as a liquid crystal display and various indication lamps. The display 4 displays an image corresponding to an image signal input from the controller 5, and turns on the indication lamps in accordance with a signal input from the controller 5. The display 4 further includes a speaker so that the speaker outputs a sound and/or a voice message corresponding to a sound signal input from the controller 5.

The controller 5 is a computer so that the controller 5 includes a CPU, a RAM, a ROM, a flash memory, an I/O device and the like. The CPU executes various process according to programs stored in the ROM. The controller 5 provides to optically measure a pulse wave in a tip of a finger of a human body with using the optical sensor 2. Further, the controller 5 executes a blood constituent concentration measurement process for measuring the blood constituent concentration based on the detected pulse wave.

Figure 2:
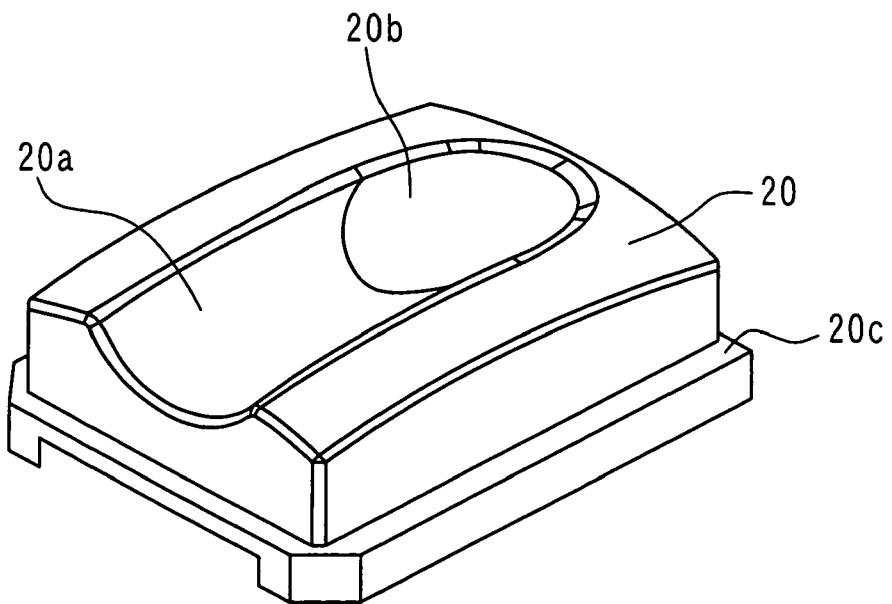
FIG. 2 is a diagram showing an optical sensor in the detector.
Figure 3:
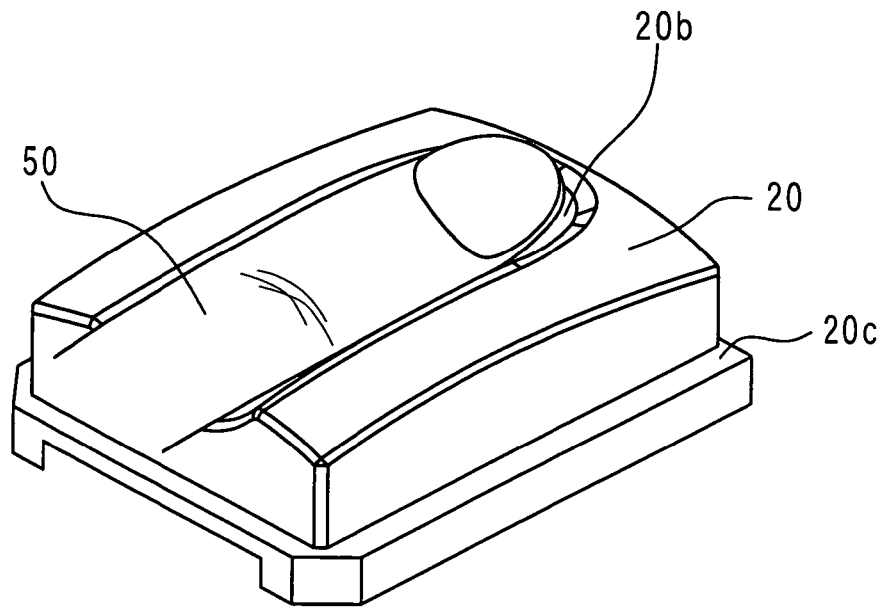
FIG. 3 is a diagram showing a finger of a user arranged in concavities of the optical sensor.
Figure 4:
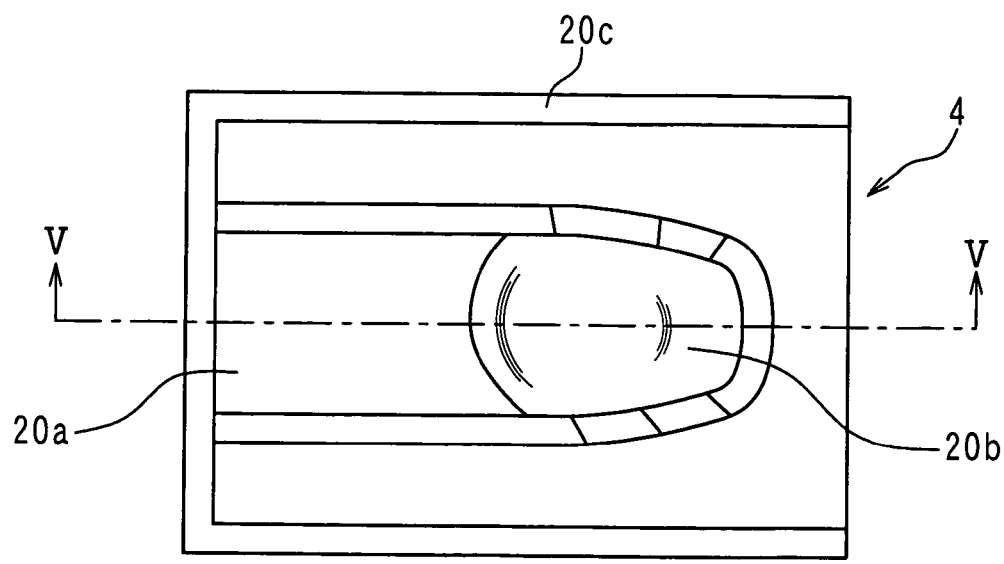
FIG. 4 is a diagram showing an upper plan view of the optical sensor.

The operation of the optical sensor 2 will be explained as follows with reference to FIGS. 2 to 5. FIG. 2 shows the optical sensor 2, and FIG. 3 shows a state that a finger of a user is mounted on the optical sensor 2. FIG. 4 shows a plan view of the optical sensor 2, and FIG. 5 shows a cross sectional view of the sensor 2.

The sensor 2 includes a casing 20 and a bottom element 20c. A first concavity 20a and a second concavity 20b are formed on the surface of the casing 20. A user puts his finger 50 in the first and second concavities 20a, 20b. When the finger of the user is mounted in the concavities 20a, 20b, as shown in FIG. 3, the finger 50 is restricted from moving in a right-left direction of the casing 20 since the concavities 20a, 20b hold the finger 50.

The first concavity 20a as a finger holding guide for a base of the finger 50 faces the base of the finger 50. The second concavity 20b as an optical window faces a pad of a tip of the finger 50. Here, the finger 50 is an example of a detection part of the human body. The optical window 20b is made of translucent material such as glass and resin. Other portions of the casing 20 including the finger holding guide 20a and the bottom element 20c are made of material not having translucent property such as resin. Alternatively, transmittance of light in the portions of the casing 20 including the finger holding guide 20a and the bottom element 20c is lower than that of the optical window 20b.

Figure 5:
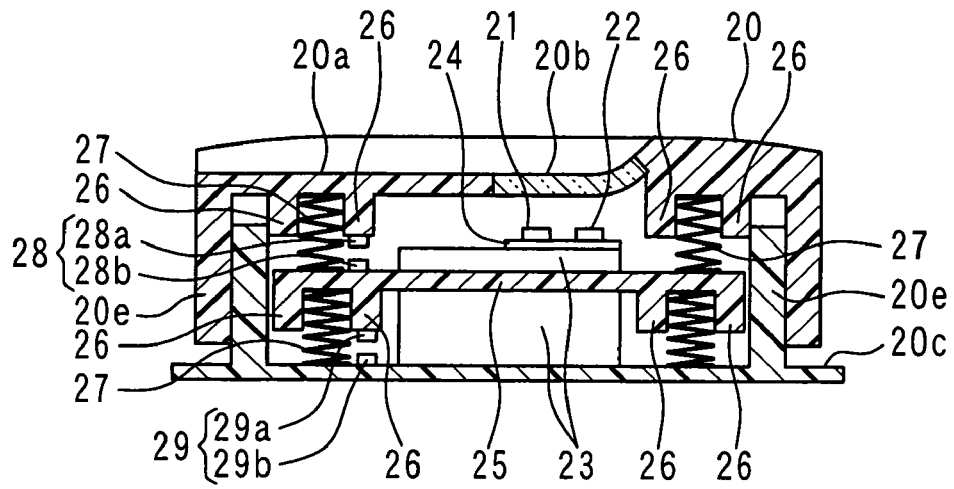
FIG. 5 is a diagram showing a cross sectional view of the sensor taken along line V-V in FIG. 4.

As shown in FIG. 5, a sidewall 20e for surrounding a center of the bottom element 20c is formed on an upper side of the bottom element 20c. A case 23 accommodates a detection circuit (not shown), and is arranged at the center of the bottom element 20c. A substrate 24 is formed on the upper side of the case 23. The light emitting device 21 and the light receiving device 22 are mounted on the substrate 24. The substrate 24 is fixed on the case 23 such that the light emitting device 21 and the light receiving device 22 are disposed under the optical window 20b. Accordingly, when the finger 50 is mounted in the concavities 20a, 20b, the pad of the finger tip faces the light emitting device 21 and the light receiving device 22 via the optical window 20b.

The light emitting device 21 includes multiple light emitting elements such as LED. The controller 5 controls each light emitting element to emit first homogeneous light as single light having a first wavelength such as 870 nm and second homogeneous light as single light having a second wavelength such as 1300 nm toward the finger tip.

The light receiving device 22 includes a photo diode or the like. The light receiving device 22 detects light amount of light, which penetrates the finger tip and outputs toward the light receiving device 22 when the light emitting device 21 emits light toward the finger tip. When the detected light amount is large, the light receiving device 22 outputs a large output voltage as an output signal to the controller 5.

When the light from the light emitting device 21 is irradiated on the finger tip, the light reaches a smaller artery, which passes in the finger tip as a detection portion. The light irradiated on the smaller artery is absorbed in blood constituent flowing in the smaller artery. Here, the blood constituent is, for example, hemoglobin, alcohol in blood, and other constituent in blood, a concentration of which is changed due to alcohol concentration in blood. Rest of the light reflects on body tissue so that the rest of the light is scattered. A part of the scattered light is received by the light receiving device 22. Since the smaller artery pulsates, the amount of the blood constituent in the smaller artery is changed in waves. Accordingly, the amount of light to be absorbed in the blood constituent is also changed according to heat beat. As a result, the output signal of the light receiving device 22 is changed according to the pulsation of the smaller artery. Thus, the light receiving device 22 detects the pulse wave in the finger tip with an optical method, and outputs the signal to the controller 5, the signal changing in accordance with measurement result.

A stay 25 is arranged between the bottom element 20c and the casing 20. Multiple spring guides 26 are formed under the stay 25. Multiple springs 27 are arranged between the bottom element 20c and the stay 25 so as to be sandwiched by the spring guides 26. Similarly, multiple spring guides 26 are formed under the casing 20. Multiple springs 27 are arranged between the bottom element 20c and the casing 20 so as to be sandwiched by the spring guides 26.

When the user puts the finger 50 on the concavities 20a, 20b of the casing 20, each spring 27 is deformed so that the casing 20 is displaced downward.

Movable contacts 28a, 28b are arranged on the bottom of the casing 20 and the top of the stay 25, which faces the bottom of the casing 20. The movable contacts 28a, 28b provides a switch 28. Similarly, movable contacts 29a, 29b are arranged on the bottom of the stay 25 and the top of the bottom element 20c, which faces the bottom of the stay 25. The movable contacts 29a, 29b provide another switch 29.

The spring 27 between the casing 20 and the stay 25 has elasticity, which is different from the spring 27 between the stay 25 and the bottom element 20c. Specifically, the spring 27 between the casing 20 and the stay 25 applies elastic force to the switch 28 such that the switch 28 turns on when load of the finger 50 to the concavities 20a, 20b is equal to or larger than a first threshold. The spring 27 between the stay 25 and the bottom element 20c applies elastic force to the switch 29 such that the switch 29 turns on when load of the finger 50 to the concavities 20a, 20b is equal to or larger than a second threshold, which is larger than the first threshold. Thus, when the load to the concavities 20a, 20b is equal to or larger than the first threshold, the switch 28 switches from an off state to an on state. When load to the concavities 20a, 20b is equal to or larger than the second threshold, the switch 29 switches from an off state to an on state. Accordingly, switching mechanism of the optical sensor 2 is a two-step push switch.

When the pulse wave is measured, and the pushing force of the finger 50 applied to the concavities 20a, 20b is weak, the intensity of light received by the light receiving device 21 is weak, so that the pulse wave is not measured with high accuracy. When the pushing force of the finger 50 applied to the concavities 20a, 20b is strong, a blood vessel is crushed, so that the pulse wave is not measured accurately.

The blood constituent concentration detector measures the blood constituent concentration based on measurement of the pulse wave under a condition that the load to the concavities 20a, 20b is controlled to be in a predetermined range. Specifically, the pulse wave is measured under a condition that the load to the concavities 20a, 20b is equal to or larger than the first threshold and smaller than the second threshold.

The first and second thresholds are set in a following manner.

Figure 6:
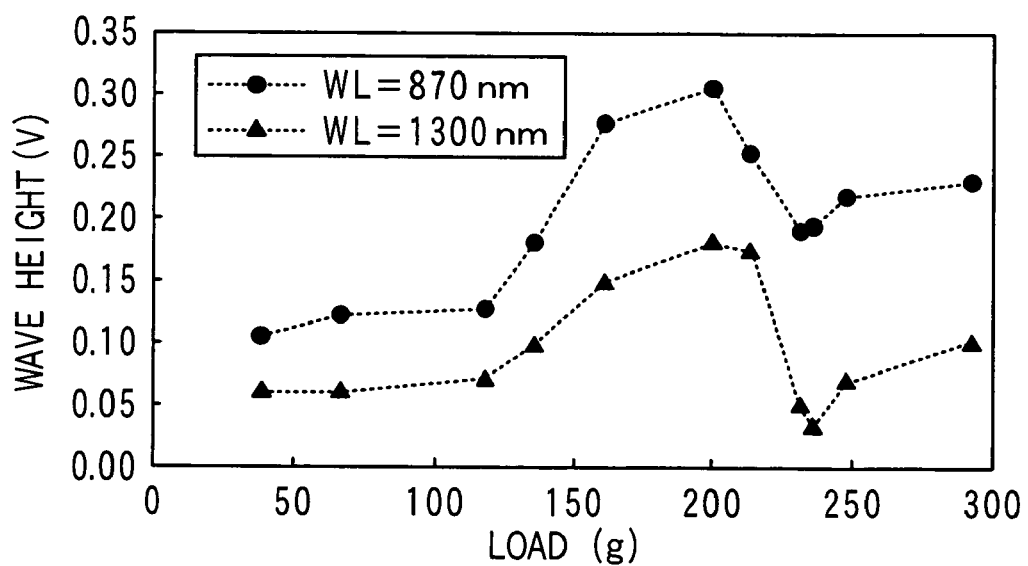
FIG. 6 is a graph showing wave heights of pulse wave signals detected by two different wavelength of light when a load to a detection portion is changed.

FIG. 6 shows a wave height of the pulse wave when the light having the wavelength of 870 nm is irradiated on the detection portion of the use, and the load to the concavities 20a, 20b is changed. Further, FIG. 6 shows a wave height of the pulse wave when the light having the wavelength of 1300 nm is irradiated on the detection portion of the use, and the load to the concavities 20a, 20b is changed. A curve representing the wavelength of 870 nm and a curve representing the wavelength of 1300 nm are obtained from the same detection portion of the same user at the same time.

As shown in FIG. 6, even when the user is same, the wave height of the pulse wave depends largely on the wavelength of the light for measurement and on the load to the concavities 20a, 20b. Further, the wave height of the pulse wave is largely changed temporarily in accordance with physiological phenomena of the user such as breath and blood pressure. Here, the wave height of the pulse wave is defined as a change amount of the pulse wave signal between a minimum value and a maximum value in one wave.

However, according to the inventors' experiment, a ratio of wave height in the pulse wave signals obtained by two different wavelengths from the same user at the same time (more specifically, at the same pulsation) is constant without depending on the blood pressure and the breath of the user. Thus, the wave height ratio of the pulse wave signals measured with using two different wavelengths provides an index of the blood constituent concentration. Thus, the influence of change of the blood pressure and breath is reduced.

Further, according to the inventors' experiment, when light having a specific wavelength is used, the wave height is sensitively changed by the concentration of a specific blood constituent. Specifically, some light having a specific wavelength is much affected by the concentration of a specific blood constituent. Some light having another specific wavelength is not substantially affected by the concentration of the specific blood constituent. For example, there is a specific wavelength of light, which sensitively responds to the concentration of alcohol in blood. There is another specific wavelength of light, which does not sensitively respond to the concentration of alcohol in blood.

In view of the above characteristics of light, the blood constituent concentration detector measures a blood constituent concentration based on the wave height ratio the two pulse wave signals detected by using two wavelengths of light.

Figure 7:
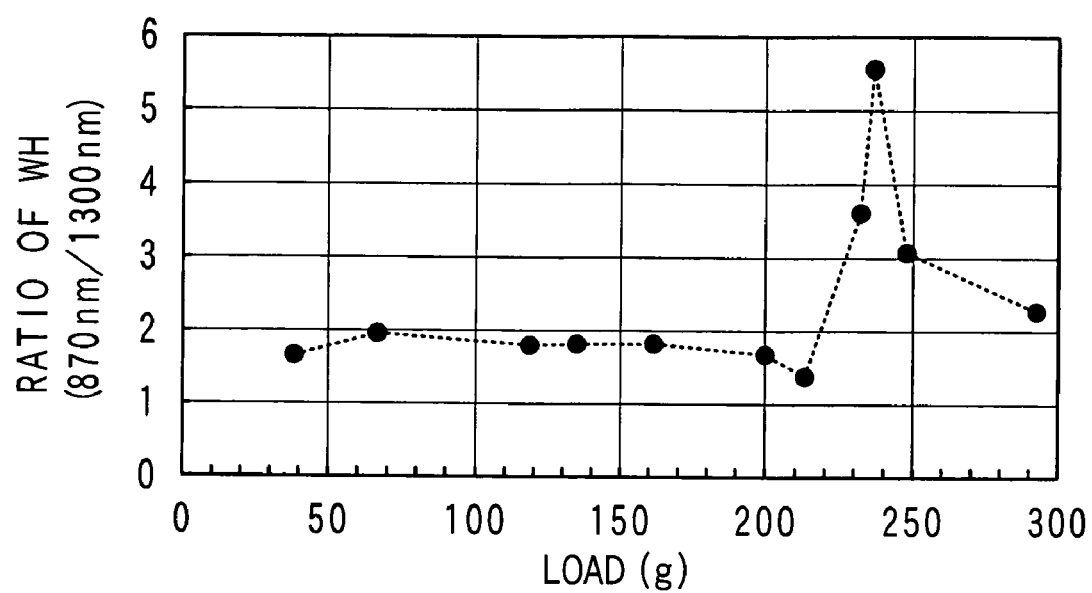
FIG. 7 is a graph showing a wave height ratio of the pulse wave signals when the load is changed.

FIG. 7 shows a curve of the ratio of wave height of the pulse wave between two wavelengths, which represents a ratio between 870 nm-measurement signal and 1300 nm-measurement signal. As shown in FIG. 7, when the load to the concavities 20a, 20b is in a range between 100 grams and 200 grams, the wave height ratio is substantially constant, i.e., stable. When the load is out of a range between 100 grams and 200 grams, the wave height ratio is not stable. Accordingly, it is preferable to measure the pulse wave for detecting the blood constituent concentration under a condition that the load to the concavities 20a, 20b is in a range between 100 grams and 200 grams.

Figure 8:
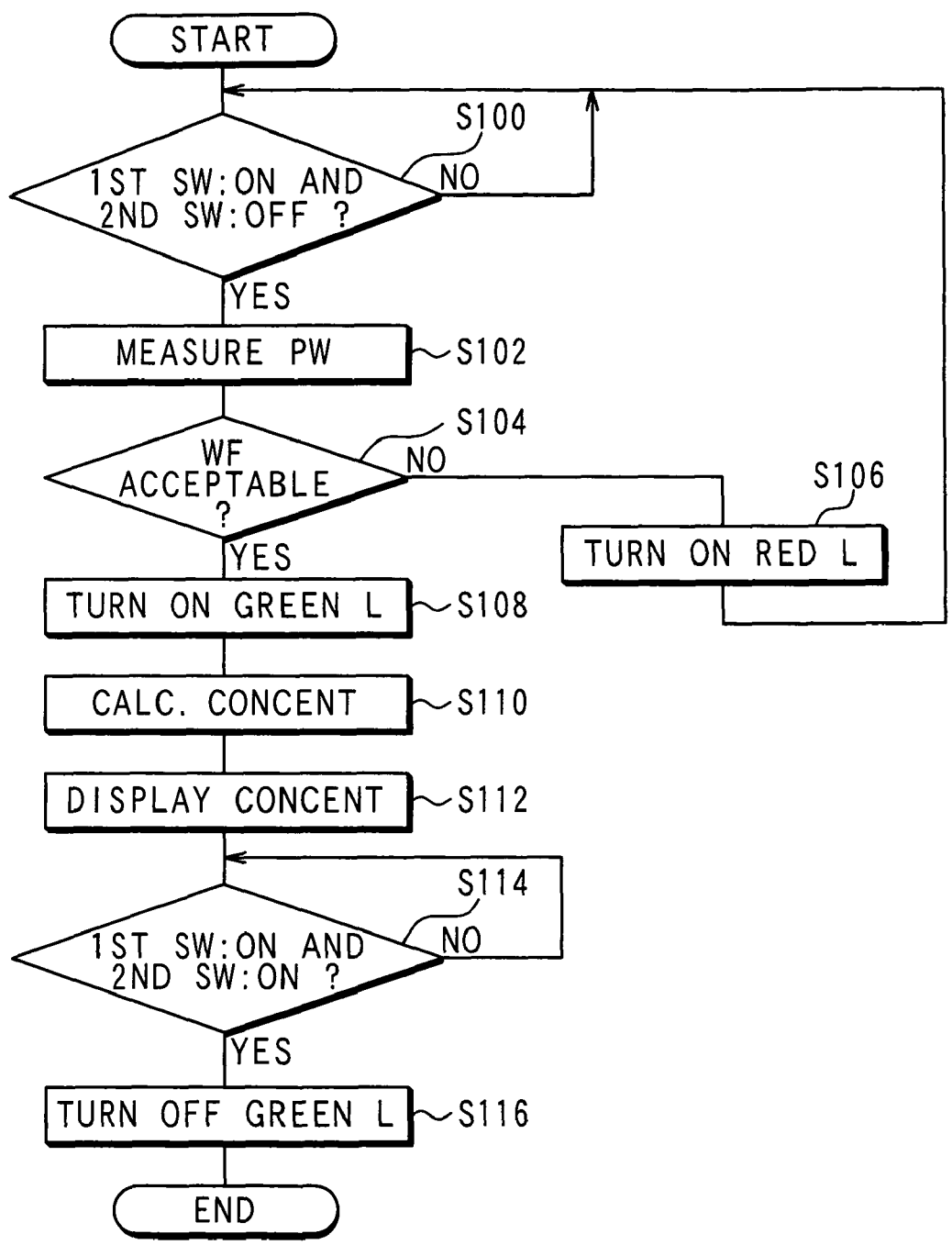
FIG. 8 is a flowchart of a controller in the detector.

FIG. 8 shows a flowchart of a process executed by the controller 5. When the user operates the operation input device 3, the operation input device 3 inputs a signal for instructing to start the blood constituent concentration measurement process. The controller 5 starts to execute the process in FIG. 8.

In Step S100, the controller determines whether a pressure of the finger 50 is in a predetermined range for starting the measurement. Specifically, the user puts the finger 50 in the concavities 20a, 20b with appropriate strength so that the switch 28 turns on, and the switch 29 turns off. Based on the on-state of the switch 28 and the off-state of the switch 29, the controller determines that the pushing force of the finger 50 is in a predetermined range. More specifically, the controller 5 determines whether the load is equal to or larger than the first threshold and smaller than the second threshold.

Here, when the load to the concavities 20a, 20b is small so that the load is smaller than the first threshold, or when the load to the concavities 20a, 20b is large so that the load is larger than the second threshold, the determination in Step S100 is "NO." In this case, Step S100 is repeated.

Here, although not shown in FIG. 8, when the load to the optical window 20b is smaller than the first threshold, a voice message such as "please put your finger a little stronger" is output. When the load to the optical window 20b is larger than the second threshold, another voice message such as "please put your finger a little weaker" is output.

When the user puts the finger in the concavities 20a, 20b with appropriate force so that the switch 28 turns on and the switch 29 turns off, the determination in Step S100 is "YES." Then, in Step S102, the pulse wave is measured. Specifically, the pulse wave is measured with using the light having the first wavelength, and then, the pulse wave is measured with using the light having the second wavelength. During a predetermined measurement time such as five seconds, the measurement with using the first wavelength and the measurement with using the second wavelength are alternately repeated. A period for measuring the pulse wave with using each wavelength is sufficiently shorter than the predetermined measurement time. For example, each period is one-tenth of the measurement time. Further, the period is sufficiently shorter than a period of one pulse beat of an ordinary human. For example, the period for each measurement is one-tenth of the one pulse beat period. Accordingly, the period is, for example, 50 milliseconds. Thus, the pulse wave can be measured with using two wavelengths almost simultaneously during one pulse beat.

Next, in Step S104, the controller 5 determines whether the waveform measured is allowable, i.e., acceptable. Specifically, based on a pulse signal measured with using the first wavelength and another pulse signal measured with using the second wavelength, which are chronologically stored in the controller 5, the wave height and a time interval of a pulse beat in one wave of each pulse signal corresponding to the one pulse beat are calculated. Multiple calculated time intervals of the pulse beat are chronologically stored. The wave height is defined as a difference between the maximum value and the minimum value of each signal. The time interval of the pulse beat is specified as a time interval between two peaks of adjacent two waves in each signal. The controller 5 determines whether the specified wave height and the time interval of the pulse beat are disposed in an appropriate range of a human.

When the wave height and the time interval are not in the appropriate range for the human, the determination in Step S104 is "NO." In this case, in Step S106, a red lamp representing measurement failure turns on. Further, a voice message showing the measurement failure is output from a speaker. Then, it returns to Step S100.

When the wave height and the time interval are in the appropriate range for the human, the determination in Step S104 is "YES." In this case, in Step S108, a green lamp representing measurement success turns on. Further, a voice message showing the measurement success is output from the speaker.

Then, in Step S110, the blood constituent concentration is calculated. Specifically, the ratio of wave heights in the same pulse beat is calculated according to the wave heights of two pulse wave signals with using two wavelengths of light calculated in Step S102. The concentration of a blood constituent such as hemoglobin, alcohol in blood, and other constituent in blood, a concentration of which is changed due to alcohol concentration in blood, is calculated based on the wave height ratio.

In Step S112, the calculated blood constituent concentration is displayed. Specifically, the wave height ratio calculated in Step S110 and representing an index of the concentration of the blood constituent is shown on a display screen of the display 4.

Then, in step SW114, the controller 5 determines based on the state of the switches 28, 29 whether the measurement ends. Specifically, the controller 5 determines that the controller 5 ends to measure the blood constituent concentration when both of the switches 28, 29 turn on.

When both of the switches 28, 29 do not turn on, the determination in Step S114 is "NO." It returns to Step S114. When the user puts the finger 50 in the concavities 20a, 20b strongly so that the load to the concavities 20a, 20b exceeds the second threshold, the switches 28 and 29 turn on. Then, the determination in Step S114 is "YES." Then, in Step S118, the measurement process for the blood constituent concentration ends, Thus, the display of the blood constituent concentration and the measurement of the pulse wave with using the optical sensor 2 are stopped, and the green lamp showing the measurement success turns off. Thus, the process ends.

The controller 5 determines whether the load to the concavities 20a, 20b is equal to or larger than the first threshold, and smaller than the second threshold, which is larger than the first threshold. When the controller 5 determines that the load to the concavities 20a, 20b is equal to or larger than the first threshold, and smaller than the second threshold, the pulse wave is measured. Thus, the blood constituent concentration is measured accurately.

Here, it is preferable that the first threshold is set to be 100 grams, and the second threshold is set to be 200 grams.

The determination of the load to the concavities 20a, 20b is performed based on the state of the switches 28, 29. Specifically, the device includes the first switch 28 and the second switch 29. The first switch 28 turns on when the load is equal to or larger than the first threshold, and the second switch 29 turns on when the load is equal to or larger than the second threshold.

Further, the controller 5 determines whether the waveform of the pulse wave is appropriate. When the controller 5 determines that the waveform of the pulse wave is not appropriate, the controller 5 informs the user of the measurement failure of the pulse wave. When the controller 5 determines that the waveform of the pulse wave is appropriate, the controller 5 informs the user of the measurement success of the pulse wave.

When the measurement of the pulse wave ends, and the controller 5 determines that the load to the concavities 20a, 20b is equal to or larger than the second threshold, the process for measuring the concentration of blood constituent ends. Thus, the user can end the process only by pushing the detection portion so that the load to the concavities 20a, 20b exceeds the second threshold after the pulse wave is measured.

(Second Embodiment)

Figure 9:
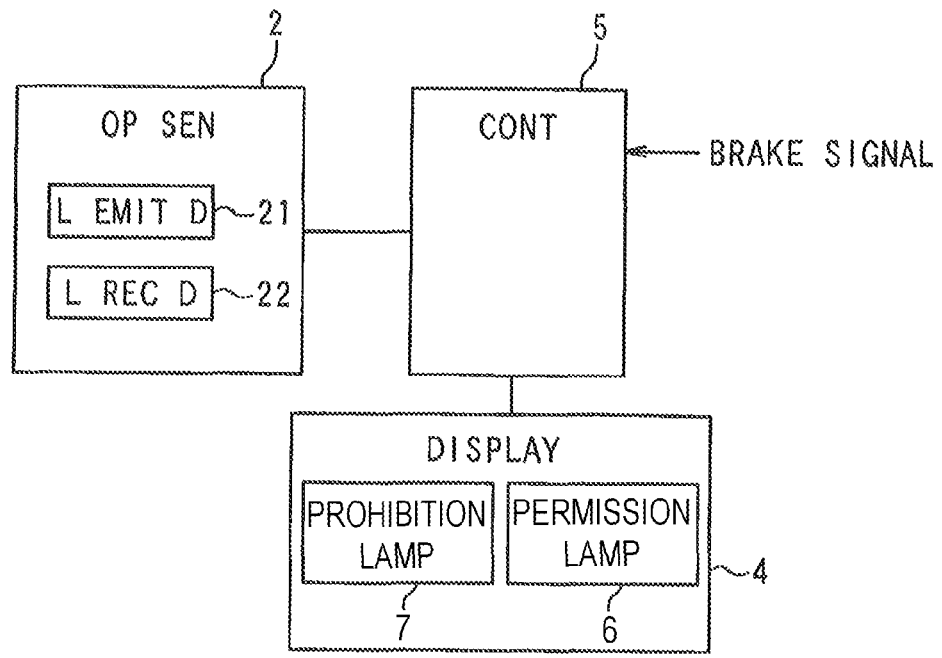
FIG. 9 is a diagram showing a starter according to a second embodiment.

FIG. 9 shows a starter for a transporter. The starter is suitably used for a vehicle, and mounted on the vehicle. The starter verifies an electronic key owned by a driver. Further, the starter switches a power source position and controls to start an engine of the vehicle with using a combination of a starter switch operation and a brake operation. The starter switch starts the engine. The starter further includes a function to measure an alcohol concentration in blood of the driver with measuring the pulse wave of the driver in an optical manner, a function to determine based on a fact that the alcohol concentration is smaller than a predetermined standard whether the driver is drunk, and a function to start the engine when the controller determines that the driver is not drunk.

The starter includes the optical sensor 2, the display 4 and the controller 5. The display 4 includes a permission lamp 6 for showing driving permission and a prohibition lamp 7 for showing driving prohibition. Each lamp is arranged in a meter or the like. The lamps turns on or off in accordance with a signal from the controller 5. A brake signal is input into the controller 5. The brake signal shows a state of a brake of the vehicle.

Figure 10:
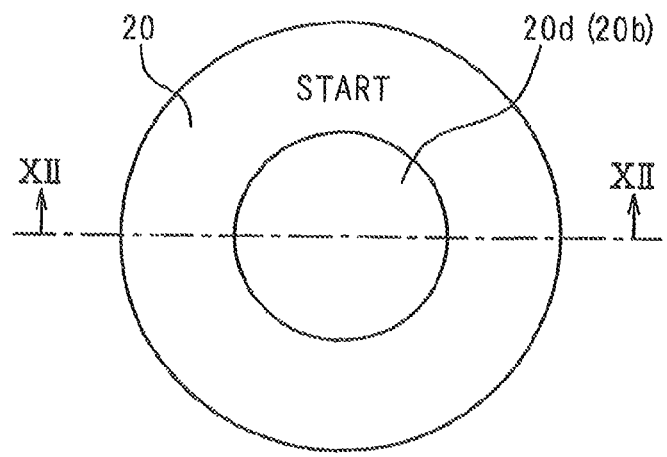
FIG. 10 is a diagram showing an optical sensor in the starter.
Figure 11:
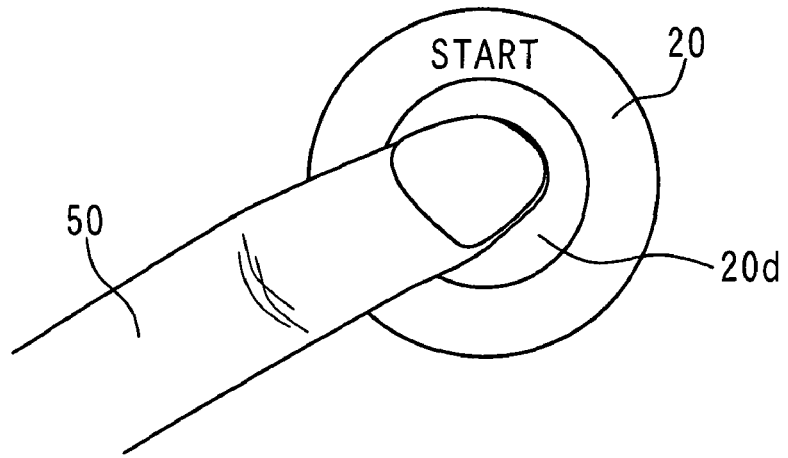
FIG. 11 is a diagram showing a finger arranged on the optical sensor.
Figure 12:
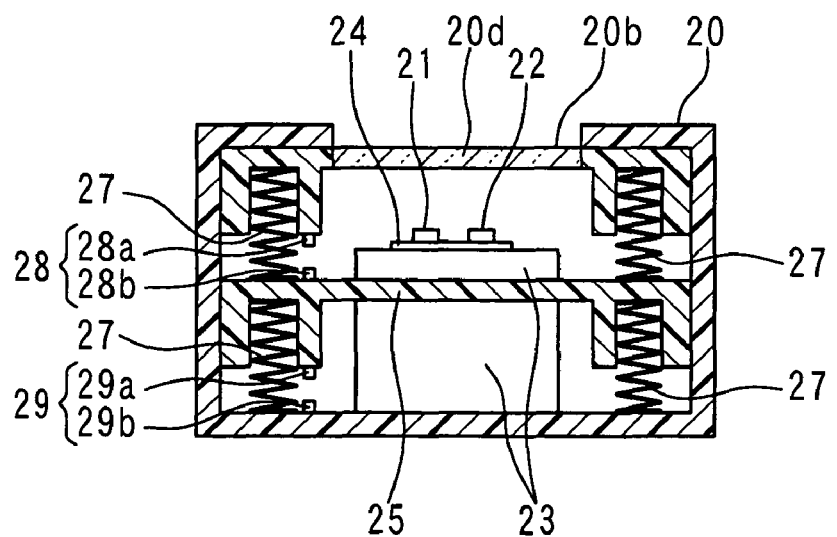
FIG. 12 is a diagram showing a cross sectional view of the optical sensor taken along line XII-XII in FIG. 10.

The optical sensor 2 will be explained with reference to FIGS. 10 to 12. FIG. 10 is a front view of the optical sensor 2. FIG. 11 shows the finger 50 mounted on the optical sensor 2. FIG. 12 is a cross sectional view showing the optical sensor 2 taken along line XII-XII.

As shown in FIG. 10, the optical sensor 2 includes the casing 20 and an operation element 20d. The operation element 20d includes the optical window 20b for measuring the pulse wave of the finger 50 in an optical manner. The operation element 20d functions as a detection portion for measuring the alcohol concentration in blood and a starter switch for starting the engine of the vehicle. Accordingly, the optical sensor 2 is preferably disposed near a driver seat. For example, the sensor 2 is arranged on an instrumental panel. Here, the optical window 20b is made of translucent material such as glass and resin. The casing 20 is made of material not having translucent property such as resin.

As shown in FIG. 11, when the driver puts the finger 50 on the operation element 20d having a circular shape with predetermined force so that the driver operates the starter switch of the engine, the light emitting device 21 emits light having two different wavelengths. Specifically, the light emitting device 21 irradiates the light on the finger 50 via the optical window 20b. Then, the pulse wave is measured so that the alcohol concentration in blood of the driver is measured based on measurement of the pulse wave.

As shown in FIG. 12, the case 23 for accommodating the detection circuit (not shown) is arranged in the casing 20. The substrate 24 is arranged on the top of the case 23. The light emitting device 21 and the light receiving device 22 are mounted on the substrate 24. The substrate 24 is fixed on the case 23 such that the light emitting device 21 and the light receiving device 22 are disposed under the optical window 20b. Accordingly, when the finger 50 is disposed in a concavity, the pad of the finger tip faces the light emitting device 21 and the light receiving device 22 through the optical window 20b.

The stay 25 is disposed between the bottom of the casing 20 and the operation element 20d. Multiple spring guides 26 are formed under the stay 25. Multiple springs 27 are arranged between the bottom of the casing 20 and the stay 25 such that the springs 27 are supported by the spring guides 26. Similarly, multiple spring guides 26 are formed under the operation element 20d. Multiple springs 27 are formed between the operation element 20d and the bottom of the casing 20 such that the springs 27 are supported by the spring guides 26.

When the driver puts the finger 50 on the operation element 20d, each spring 27 is deformed so that the operation element 20d is displaced downward.

Further, the movable contacts 28a, 28b are arranged on the bottom of the casing 20 and the top of the stay 25, which faces the bottom of the casing 20. The movable contacts 28a, 28b provides a switch 28. Similarly, movable contacts 29a, 29b are arranged on the bottom of the stay 25 and the top of the bottom element 20c, which faces the bottom of the stay 25. The movable contacts 29a, 29b provide another switch 29.

The spring 27 between the casing 20 and the stay 25 has elasticity, which is different from the spring 27 between the stay 25 and the bottom element 20c. Specifically, the spring 27 between the casing 20 and the stay 25 applies elastic force to the switch 28 such that the switch 28 turns on when load of the finger 50 to the concavities 20a, 20b is equal to or larger than a first threshold. The spring 27 between the stay 25 and the bottom element 20c applies elastic force to the switch 29 such that the switch 29 turns on when load of the finger 50 to the concavities 20a, 20b is equal to or larger than a second threshold, which is larger than the first threshold. Thus, when the load to the concavities 20a, 20b is equal to or larger than the first threshold, the switch 28 switches from an off state to an on state. When load to the concavities 20a, 20b is equal to or larger than the second threshold, the switch 29 switches from an off state to an on state. Accordingly, switching mechanism of the optical sensor 2 is a two-step push switch.

The blood constituent concentration detector measures the blood constituent concentration based on measurement of the pulse wave under a condition that the load to the operation element 20d is controlled to be in a predetermined range. Specifically, the pulse wave is measured under a condition that the load to the operation element 20d is equal to or larger than the first threshold and smaller than the second threshold.

The starter verifies an electronic key owned by a driver. Further, the starter switches a power source position and controls to start an engine of the vehicle with using a combination of a starter switch operation and a brake operation.

When the starter switch is operated, a fundamental operation will be explained as follows. First, when the driver operates the starter switch under a condition that the engine of the vehicle stops and the driver does not step on the brake, the power position is changed from an off-state, an ACC position, an IG on position to the off-state at each time when the switch is operated. AT this time, the engine does not start.

When the driver steps on the brake, and operates the starter switch, the engine starts and the power position is switched to the IG on position.

When the engine runs, and the driver operates the starter switch, the engine stops, and the power position is switched to the off-state even when the driver steps on or does not step on the brake.

Thus, the starter switches a power source position and controls to start an engine of the vehicle with using a combination of a starter switch operation and a brake operation. Further, the starter measures the alcohol concentration in blood with measuring the pulse wave of the driver in an optical manner, and controls to start and stop the engine of the vehicle based on the determination whether the alcohol concentration in blood is smaller than the reference standard.

Figure 13:
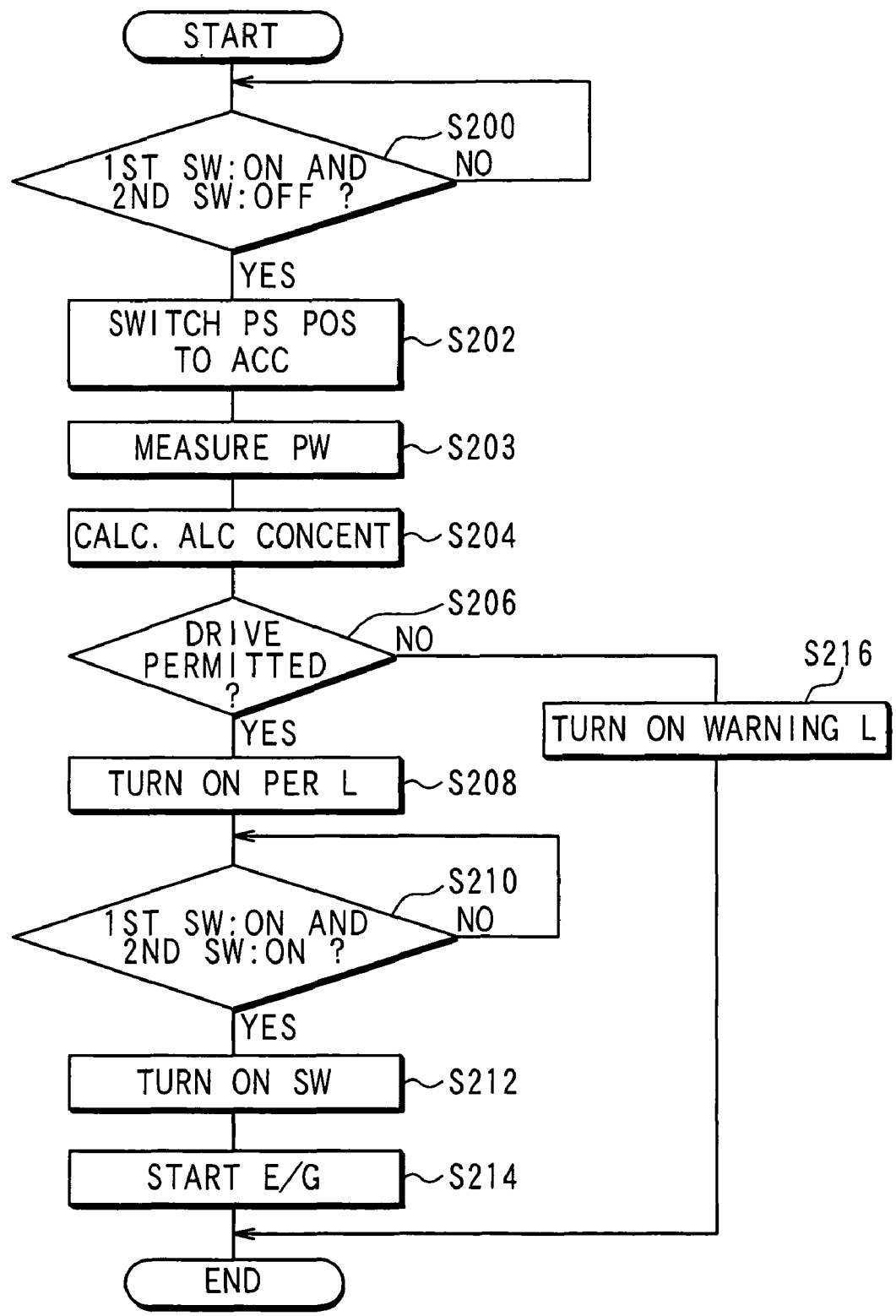
FIG. 13 is a flowchart of a controller in the starter.

FIG. 13 shows an engine start control process for controlling to start or stop engine based on measurement of the alcohol concentration in blood of the driver. Here, the power source position is in an off-state. When the electronic key owned by the driver is verified, the verification is successful, and the diver steps on the brake, the controller 5 executes the process in FIG. 13.

In Step S200, the controller determines whether a pressure of the finger 50 is in a predetermined range for starting the measurement. Specifically, the user puts the finger 50 on the operation element 20d with appropriate strength so that the switch 28 turns on, and the switch 29 turns off. Based on the on-state of the switch 28 and the off-state of the switch 29, the controller determines that the pushing force of the finger 50 is in a predetermined range. More specifically, the controller 5 determines whether the load is equal to or larger than the first threshold and smaller than the second threshold.

When the load to the operation element 20d is small so that the load is smaller than the first threshold, or when the load to the operation element 20d is large so that the load is larger than the second threshold, the determination in Step S100 is "NO." In this case, Step S200 is repeated.

Here, although not shown in FIG. 8, when the load to the operation element 20d is smaller than the first threshold, a voice message such as "please put your finger a little stronger" is output. When the load to the operation element 20d is larger than the second threshold, another voice message such as "please put your finger a little weaker" is output.

When the user puts the finger on the operation element 20d with appropriate force so that the switch 28 turns on and the switch 29 turns off, the determination in Step S200 is "YES." Then, in Step S202, the power source position is switched to the ACC position.

Then, in Step S203, the pulse wave is measured, similar to Step S102 in FIG. 8. Specifically, the pulse wave is measured with using the light having the first wavelength, and then, the pulse wave is measured with using the light having the second wavelength. During, a predetermined measurement time such as five seconds, the measurement with using the first wavelength and the measurement with using the second wavelength are alternately repeated. Thus, the pulse wave is measured with using two wavelengths almost simultaneously during one pulse beat.

Then, in Step S204, similar to Step S110 in FIG. 8, the alcohol concentration in blood is calculated. Specifically, the ratio of wave heights in the same pulse beat is calculated according to the wave heights of two pulse wave signals with using two wavelengths of light calculated in Step S203. The concentration of alcohol in blood is calculated based on the wave height ratio.

Then, in Step S206, driving permission determination is performed. Specifically, the controller 5 determines whether the wave height ratio is equal to or larger than a standard wave height ratio, which is an example value of drinking drive standard. Based on the determination, the controller 5 determines whether driver can drive the vehicle.

When the wave height ratio is smaller than the standard wave height ratio, i.e., when the controller 5 determines that the drive of the driver is permitted, the determination in Step S206 is "YES." Then, in Step S208, a permission lamp 6 showing the drive permission turns on. The permission lamp 6 is arranged on the display 4.

Then, in Step S210, the controller 5 determines whether the controller 5 switches to start the engine. Specifically, the controller determines whether both of the switches 28, 29 turn on since the driver puts the finger 50 on the operation element 20d strongly. Based on the determination relating to the switches 28, 29, the controller determines whether the controller starts the engine.

Here, when the load to the operation element 20*d* is small so that both of the switches 28, 29 do not turn on, the determination in Step S210 is "NO." In this case, Step S210 is repeated.

When the driver puts the finger on the operation element 20*d* strongly so that both of the switches 28, 29 turn on, the determination in Step S210 is "YES." Then, in Step S212, the controller 5 switches on an engine start switch for starting the engine of the vehicle. Specifically, the controller 5 transmits a signal for starting the engine to the engine start switch (not shown). Thus, in Step S214, the engine starts.

However, when the alcohol concentration in blood of the driver is calculated, and the wave height ratio calculated from two wave heights of the pulse wave signals detected by two wavelengths of light is smaller than the wave height ratio standard, the determination in Step S206 is "NO." Then, in step S216, the warning lamp 7 in the display 4 showing driving prohibition turns on. Thus, an interlock function, as a fail-safe function for prohibiting from starting the engine of the vehicle works on. Then, the process ends.

In the above system, the pulse wave is measured under a condition that the load to the operation element 20*d* is equal to or larger than the first threshold, and smaller than the second threshold. Based on the measured pulse wave, the alcohol concentration in blood of the driver is detected. Thus, the alcohol concentration in blood is accurately measured.

Further, the controller 5 determines based on the determination that the alcohol concentration in blood is smaller than the standard whether the start of the engine of the vehicles is permitted. When the controller 5 determines that the start of the engine is permitted, and the load to the operation element 20*d* is equal to or larger than the second threshold, the pushing operation to the operation element 20*d* provides starting operation of the starter switch, so that the engine starts to operate. Thus, when the controller 5 determines that the alcohol concentration in blood is smaller than the reference standard, and further, driver pushes the operation element 20*d* strongly so that the load to the operation element 20*d* is equal to or larger than the second threshold, the engine of the vehicle starts.

(Other Embodiments)

In the first and second embodiments, the blood constituent concentration is detected by measuring the pulse wave in a part of a human body in the optical manner when the part of the body is pressed to the detection portion. Alternatively, the blood constituent concentration may be detected by measuring other objects.

Further, in the first and second embodiments, two different lights having two different wavelengths are irradiated on a part of the body. The reflected light on the part of the body and the transmitted light through the part of the body are received. Then, the wave height of each wavelength is calculated. Based on the wave height ratio of the two wave heights corresponding to two wavelengths of lights, the blood constituent concentration, i.e., the alcohol concentration in blood is measured. Alternatively, for example, only one type of light having one wavelength may be irradiated on the part of the human body, and the reflected light on the part of the body and the transmitted light through the part of the body may be received. The blood constituent concentration, i.e., the alcohol concentration in blood may be measured by detecting deviation of the received light intensity caused by the pulse wave. Alternatively, three different lights having three different wavelengths may be irradiated on a part of the body. The reflected light on the part of the body and the transmitted light through the part of the body may be received. Then, the wave height of each wavelength may be calculated. Based on the wave height ratio of the two wave heights corresponding to two wavelengths of lights among three wavelengths of lights, the blood constituent concentration, i.e., the alcohol concentration in blood maybe measured. In this case, two wave heights are selected among three wave heights.

In the first and second embodiments, the blood constituent concentration detector includes the switch 28 which turns on when the load to the detection portion is equal to or larger than the first threshold, and the switch 29 which turns on when the load to the detection portion is equal to or larger than the second threshold. Based on the state of each switch 28, 29, the detector determines whether the load to the detection portion is equal to or larger than the first threshold, and smaller than the second threshold. Alternatively, for example, the detector may include a sensor for detecting the load to the detection portion, and based on a signal from the sensor, the detector may determine whether the load to the detection portion is equal to or larger than the first threshold, and smaller than the second threshold.

In the first and second embodiments, the blood constituent concentration detector includes the switch 28 which turns on when the load to the detection portion is equal to or larger than the first threshold, and the switch 29 which turns on when the load to the detection portion is equal to or larger than the second threshold. When the switch 28 turns on, and the switch 29 turns off, the detector determines that the load to the detection portion is equal to or larger than the first threshold, and smaller than the second threshold. Alternatively, for example, the blood constituent concentration detector may include a switch 28 which turns off when the load to the detection portion is equal to or larger than the first threshold, and a switch 29 which turns off when the load to the detection portion is equal to or larger than the second threshold. When the switch 28 turns off, and the switch 29 turns on, the detector may determine that the load to the detection portion is equal to or larger than the first threshold, and smaller than the second threshold.

The switches 28, 29 may be a two-step push switch, which generates sensation of, for example, one click feeling when the switch switches from one state to second state. In this case, the user can easily recognize from the one click feeling that the load to the detection portion is equal to or larger than the first threshold, and smaller than the second threshold.

In the first embodiment, when the measurement of the pulse wave is proper, the detector informs the driver of proper measurement via the display and the voice message on the display 4. Alternatively, at least one of the display and the voice message may be output.

In the second embodiment, the starter controls to start the engine of the vehicle according to the operation of the driver. The starter may be used for an electric vehicle, a motorcycle, a train, an air plane, a ship, a boat or the like. Specifically, the starter may be used for a transporter so that the starter controls to start a power source such as an engine and a motor.

The concavities 20*a*, 20*b* and the operation element 20*d* correspond to the detection portion. Steps S100 and S200 correspond to a load determination element. The light emitting device corresponds to the light irradiation element. The light receiving device corresponds to the light receiving element. Steps S102, S110, S203 and S204 correspond to a measurement element. The switch 28 corresponds to the first switch, and the switch 29 corresponds to the second switch. Step S104 corresponds to a waveform determination element. Step S106 corresponds to a measurement failure informing element. Step S114 corresponds to a measurement ending element. Step S206 corresponds to a starting permission element. Steps S210 and S212 correspond to a starter.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A starter for controlling start of a power source of a transporter based on operation of a starter switch by a driver, the starter comprising:
   a detection portion having an optical window for measuring an alcohol concentration in blood of the driver in an optical manner;
   a load determination element for determining whether a load to the detection portion is equal to or larger than a first threshold, and smaller than a second threshold, wherein the second threshold is larger than the first threshold;
   a measurement element for measuring the alcohol concentration in the blood when the load determination element determines that the load to the detection portion is equal to or larger than the first threshold, and smaller than the second threshold;
   a starting permission element for determining start permission of the power source based on determination whether the alcohol concentration in the blood is smaller than a predetermined standard;
   a permission lamp for showing the start permission of the power source; and
   a starting controller for controlling the start of the power source,
   wherein the permission lamp turns on when the starting permission element determines the start permission of the power source,
   wherein, when the load determination element determines that the load to the detection portion is equal to or larger than both the first threshold and the second threshold, after the permission lamp turns on, the starting controller determines that the operation of the detection portion by the driver provides the operation of the starter switch by the driver, and
   wherein the starting controller starts the power source when the starting permission element determines the start permission of the power source, and the operation of the detection portion by the driver provides the operation of the starter switch by the driver.

2. The starter according to claim 1,
   wherein the starting controller starts the power source when the starting permission element determines the start permission, the load determination element determines that the load to the detection portion is equal to or larger than the second threshold, and the operation of the detection portion by the driver provides the operation of the starter switch by the driver.

3. The starter according to claim 1, further comprising:
   a warning lamp for showing a start prohibition,
   wherein the warning lamp turns on when the starting permission element determines the start prohibition of the power source.

4. The starter according to claim 3,
   wherein, when the load determination element determines that the load to the detection portion is equal to or larger than the first threshold, and is smaller than the second threshold, a power source position is switched to an accessory position,
   wherein the measurement element measures a pulse wave using two wavelengths of light, and calculates a ratio of wave heights in a same pulse beat of the pulse wave according to the wave heights of two pulse wave signals using two wavelengths of light, so that the measurement element measures the alcohol concentration in blood,
   wherein the starting permission element compares the ratio of wave heights with a standard wave height ratio,
   wherein, when the ratio of wave heights is smaller than the standard wave height ratio, the starting permission element determines the start permission of the power source, and
   wherein, when the ratio of wave heights is equal to or larger than the standard wave height ratio, the starting permission element determines the start prohibition of the power source.

5. The starter according to claim 1, wherein the detection portion is a starter switch for the transporter.

6. A starter for controlling start of a power source of a vehicle based on an operation of a starter switch by a driver, the starter comprising:
   a detection portion having an optical window configured to optically measure an alcohol concentration in blood of the driver;
   a load determination element configured to determine whether a load to the detection portion is either smaller than a first threshold or equal to or larger than the first threshold, and is configured to determine whether the load to the detection portion is either smaller than a second threshold or equal to or larger than the second threshold, wherein the second threshold is larger than the first threshold;
   a measurement element configured to measure the alcohol concentration in the blood when the load determination element determines that the load to the detection portion is equal to or larger than the first threshold, and smaller than the second threshold;
   a starting permission element configured to determine whether the power source may be started based on a determination as to whether the alcohol concentration in the blood is smaller than a predetermined standard, and configured to indicate when the power source may be started;
   a permission lamp configured to turn on when the starting permission element indicates that the power source may be started; and
   a starting controller configured to control a start of the power source;
   wherein the starting controller is further configured to determine that the operation of the detection portion by the driver indicates the operation of the starter switch when the load determination element determines that the load to the detection portion is equal to or larger than both the first threshold and the second threshold, after the permission lamp turns on, and wherein the starting controller is further configured to start the power source when the starting permission element indicates that the power source may be started, and when the starting controller determines that the operation of the detection portion by the driver indicates the operation of the starter switch.

7. The starter according to claim 6, further comprising:
a warning lamp configured to turn on when the starting permission element indicates that the power source may not be started.

8. The starter according to claim 6,
wherein the measurement element is configured to measure a pulse wave using two wavelengths of light, and is configured to calculate a ratio of wave heights in a same pulse beat of the pulse wave according to the wave heights of two pulse wave signals using two wavelengths of light, so that the measurement element is configured to measure the alcohol concentration in blood,
wherein the starting permission element is configured to compare the ratio of wave heights with a standard wave height ratio,
wherein the starting permission element is configured to determine that the power source may be started when the ratio of wave heights is smaller than the standard wave height ratio, and
wherein the starting permission element is configured to determine that the power source may not be started when the ratio of wave heights is equal to or larger than the standard wave height ratio.

9. The starter according to claim 6, wherein the detection portion is a starter switch for the transporter.

\* \* \* \* \*